(12) United States Patent
Breman

(10) Patent No.: US 9,080,108 B2
(45) Date of Patent: Jul. 14, 2015

(54) PROCESS FOR PRODUCING AT LEAST ONE PRODUCT FROM AT LEAST ONE GASEOUS REACTANT IN A SLURRY BED

(75) Inventor: Berthold Berend Breman, Zutphen (NL)

(73) Assignee: SASOL TECHNOLOGY (PROPRIETARY) LIMITED, Johannesburg (ZA)

( * ) Notice: Subject to any disclaimer, the term of this patent is extended or adjusted under 35 U.S.C. 154(b) by 0 days.

(21) Appl. No.: 14/124,107

(22) PCT Filed: May 30, 2012

(86) PCT No.: PCT/IB2012/052693
§ 371 (c)(1),
(2), (4) Date: Dec. 5, 2013

(87) PCT Pub. No.: WO2012/168830
PCT Pub. Date: Dec. 13, 2012

(65) Prior Publication Data
US 2014/0107232 A1    Apr. 17, 2014

Related U.S. Application Data

(60) Provisional application No. 61/493,988, filed on Jun. 7, 2011.

(30) Foreign Application Priority Data

Jun. 7, 2011  (ZA) .................................. 2011/04229

(51) Int. Cl.
| | |
|---|---|
| C07C 27/06 | (2006.01) |
| C10G 2/00 | (2006.01) |
| B01J 8/18 | (2006.01) |
| B01J 8/22 | (2006.01) |
| B01J 8/28 | (2006.01) |

(52) U.S. Cl.
CPC ............... *C10G 2/344* (2013.01); *B01J 8/1827* (2013.01); *B01J 8/1836* (2013.01); *B01J 8/22* (2013.01); *B01J 8/28* (2013.01); *C10G 2/32* (2013.01); *C10G 2/332* (2013.01); *C10G 2/342* (2013.01); *B01J 2208/00141* (2013.01); *B01J 2208/00274* (2013.01)

(58) Field of Classification Search
None
See application file for complete search history.

(56) References Cited

U.S. PATENT DOCUMENTS

| | | | |
|---|---|---|---|
| 6,117,814 | A | 9/2000 | Plecha et al. |
| 6,262,132 | B1 | 7/2001 | Singleton et al. |
| 6,638,889 | B1 | 10/2003 | Van Berge et al. |
| 6,800,664 | B1 | 10/2004 | Espinoza et al. |
| 6,914,082 | B2 | 7/2005 | Zhang et al. |
| 2003/0109590 | A1 | 6/2003 | Schweitzer et al. |

FOREIGN PATENT DOCUMENTS

| | | |
|---|---|---|
| EP | 0 450 860 A2 | 10/1991 |
| WO | 2004/101475 A1 | 11/2004 |
| WO | 2005/107935 A1 | 11/2005 |

OTHER PUBLICATIONS

Krishna, R., et al., "A strategy for scaling up the Fischer-Tropsch bubble column slurry reactor", Topics in Catalysis, vol. 26, No. 1-4, Dec. 2003, pp. 21-28.
Vandu, Chippla O., et al., "Gas-Liquid Mass Transfer in a Slurry Bubble Column at High Slurry Concentrations and High Gas Velocities", Chem. Eng. Technol., vol. 28, No. 9, 2005, pp. 998-1002.
Luo, Xukun, et al., "Maximum Stable Bubble Size and Gas Holdup in High-Pressure Slurry Bubble Columns", AIChE Journal, vol. 45, No. 4, Apr. 1999, pp. 665-680.
Behkish, Arsam, et al., "Novel correlations for gas holdup in large-scale slurry bubble column reactors operating under elevated pressures and temperatures", Chemical Engineering Journal, 115 (2006), pp. 157-171.

*Primary Examiner* — Sudhakar Katakam
(74) *Attorney, Agent, or Firm* — Ladas & Parry LLP

(57) ABSTRACT

A process for producing at least one product from at least one gaseous reactant includes feeding the gaseous reactant, as a gaseous feed or as part of a gaseous feed which is at an inlet superficial gas velocity of at least 0.5 m/s, into a vessel holding an expanded slurry bed of solid catalyst particles suspended in a suspension liquid so that the gaseous reactant can bubble upwardly through the slurry bed. The slurry bed has a catalyst loading of less than 14% by volume of degassed slurry. The gaseous reactant is allowed to react catalytically at a pressure above atmospheric pressure as the gaseous reactant bubbles upwardly through the slurry bed to produce at least one product. The product and any unreacted gaseous reactant are withdrawn from the vessel.

11 Claims, 6 Drawing Sheets

PROCESS FOR PRODUCING AT LEAST ONE PRODUCT FROM AT LEAST ONE GASEOUS REACTANT IN A SLURRY BED

RELATED APPLICATION INFORMATION

This application is a 371 of International Application PCT/IB2012/052693 filed 30 May 2012 entitled "Process For Producing At Least One Product From At One Gaseous Reactant In A Slurry Bed", which was published in the English language on 13 Dec. 2012, with International Publication Number WO 2012/168830 A1,which claims priority from South African Patent Application 2011/04229 filed 07 Jun. 2011 and U.S. Provisional Patent Application 61/493,988 filed 07 Jun. 2011, the content of which is incorporated herein by reference.

THIS INVENTION relates to a process for producing at least one product from at least one gaseous reactant in a slurry bed.

It is generally desirable to be able to increase the productivity per volume of slurry reactors so that a smaller total reactor volume is required in order to achieve the desired production capacity of the plant. It is further desirable to increase the overall production rate of products in one single reactor (i.e. the so called single reactor capacity) so that a smaller number of reactors will be required in order to achieve the desired production capacity of the plant.

Consider for example the well-known Fischer-Tropsch synthesis as operated in a slurry bubble column reactor. Regardless of whether such a reactor operates in a once-through mode or under recycle, the production rate of a single reactor can be expressed as follows:

$$SRC = \overset{\circ}{V}\left(\frac{P_{syngas}}{RT}\right)(X_{per\,pass}), \quad\quad 1$$

where SRC is the single reactor capacity, $\overset{\circ}{V}$ is the total volumetric gas flow rate into the reactor (i.e. fresh feed plus recycle), $P_{syngas}$ is the partial pressure of synthesis gas (the reagents of the synthesis) in the total feed, T is the absolute temperature in Kelvin, R is the gas constant and $\chi_{per\,pass}$ is the per pass conversion of synthesis gas expressed as a mol fraction. The above equation can be further expanded as follows:

$$SRC = u_g\left(\frac{\pi}{4}d^2\right)\left(\frac{P_{syngas}}{RT}\right)(X_{per\,pass}), \quad\quad 2$$

where $u_g$ is the inlet superficial gas velocity and d is the internal diameter of the reactor. Considering Equation 2, it is clear that the following options are available to the design engineer in order to increase the single reactor capacity of a slurry bubble column:

Increase the per pass synthesis gas conversion. However, in the Fischer-Tropsch synthesis, water (one of the products of the hydrocarbon synthesis process) causes deactivation of the catalyst. Consequently, a maximum per pass conversion is normally specified that should not be exceeded in the design of a Fischer-Tropsch slurry bubble column reactor in order to limit the water partial pressure and thereby protect the performance and lifetime of the catalyst. The exact value of the per pass conversion is catalyst dependent.

Increase the synthesis gas partial pressure in the total feed: However, there is limited scope for the design engineer to increase the concentration of synthesis gas in the total feed, as this is often determined by the configuration of an overall gas loop of which the slurry bubble column forms part. Furthermore, increasing the reactor operating pressure is an obvious way to increase the synthesis gas partial pressure in the feed, but this has significant cost implications both for the reactor and other plant equipment which may prove to be prohibitive. Higher pressures also lead to higher water partial pressures at the same per pass conversion, which may be detrimental to the catalyst.

Increase the reactor diameter: However, this will add substantially to the construction cost of the reactor. Furthermore, large scale slurry bubble column reactors are already manufactured with sizes close to the practical limit in terms of factory construction, transportation from factory to plant site, and erection.

Increase the inlet superficial gas velocity: However, as will subsequently be discussed, there are clear teachings in the prior art away from operating slurry bubble column reactors at high inlet superficial gas velocities.

The skilled person looking to increase the single reactor capacity of a slurry bubble column reactor is therefore left with limited possibilities, the most viable on the face of it being improving the resistance of the catalyst to water to allow for higher per pass conversions, or completely changing the gas loop configuration and pressure in order to increase the reactant partial pressure in the reactor feed.

EP 450860 to Exxon states that optimal performance of a slurry bubble column reactor is attained when the gas velocity is just high enough to ensure complete fluidisation of the catalyst particles. Increasing the gas velocity beyond this point will cause an undesired increase in the extent of back mixing, leading to a loss of plug flow characteristics in the reactor and resulting in lower reaction rates. It teaches that the optimum gas velocity in terms of overall reactor productivity is below 0.25 m/s. The patent further teaches that a high reaction rate per volume of reactor is undesirable, as the catalyst can easily become starved of reactants due to mass transfer limitations.

U.S. Pat. No. 6,914,082 to Conoco provides "a gas-agitated multiphase reactor system that is effective for enabling maximum reactor productivity and/or minimising reactor volume". In other words, a method is provided for maximising the productivity per unit volume of reactor. In this regard, it is shown that the reactor volumetric space-time yield improves with increasing gas velocity up until a peak value between 0.3 and 0.4 m/s, after which the reactor volumetric space-time yield declines with further increases in gas velocity. It is stated that the initial increase in reactor volumetric productivity is due to improvements in mass transfer, while the decline in productivity is due to an increase in gas hold-up with increasing gas velocity, yielding an optimum gas velocity where reactor productivity is at a maximum.

US Patent Application No 2003/0109590A1 by ENI and IFP teaches that the superficial gas velocity of a slurry bubble column reactor should preferably be less than 0.35 m/s, more preferably less than 0.30 m/s, to encourage gas transfer into the liquid phase. In other words, this application anticipates the occurrence of detrimental mass transfer limitations at gas velocities higher than about 0.35 m/s.

WO2005/107935 to Sasol Technology (Pty) Ltd discloses that, for a hydrocarbon synthesis process, a CO plus $H_2$ per pass conversions in excess of 60% is achievable when operating at inlet superficial gas velocities above 0.35 m/s in slurry reactors in which the expanded slurry bed has a length to diameter aspect ratio of less than 5. In the specific example presented in WO2005/107935, it was estimated that a per pass CO plus $H_2$ conversion of 61% is achievable when operating with a 22 volume % average catalyst concentration, an expanded slurry bed with an aspect ratio of approximately 4, a pressure of 24.7 bar and an inlet superficial gas velocity of 0.41 m/s.

There is thus a clear bias in the patent literature against operating commercial slurry bubble column reactors at high inlet superficial gas velocities, especially when the aim is to improve productivity per volume of reactor. Most prior art documents teach an optimum inlet superficial gas velocity of around 0.3 to 0.4 m/s, while others teach operation at even lower inlet superficial gas velocities. Moreover, none of the prior art documents addresses the issue of increasing the single reactor production capacities of slurry bubble column reactors.

Three phase slurry bubble columns typically feature a catalyst suspended in a suspension liquid, with the catalyst catalysing the reaction of one or more gaseous reactants fed to the reactor. The gas phase reactant(s) must be transferred from the gas phase into the liquid phase where it contacts the catalyst and are converted to one or more products. On the one hand, provided the rate of gas-liquid mass transfer is sufficiently high, the overall reaction rate can be increased by increasing the amount or the activity of the catalyst. In such a case, the reaction system is said to be under kinetic control. On the other hand, if the gas-liquid mass transfer rate is too low, an increase in the catalyst amount or activity will not significantly increase the production rate and then the system is said to be under mass transfer control. Often commercial slurry bubble column reactors operate in a regime where both kinetic and mass transfer considerations are important. Industrial slurry reactor processes for the conversion of gas phase reactants to products, such as the well-known Fischer-Tropsch synthesis, is typically operated at high pressure. When looking to increase the single reactor capacity of such slurry reactors by operating them at a combination of a high inlet superficial gas velocity and high pressure, two concerns (amongst others) surface: (i) the gas hold-up in the reactor and (ii) whether or not the mass transfer rate will be sufficient to sustain the conversion of reactants to products.

The prior art is sparse with respect to gas hold-up data at the combination of high gas velocity and high pressure. It does however allow for certain high level trends to be discerned. It is widely reported in the prior art that gas hold-up increases with increasing gas velocity (see e.g. Krishna et al., Topics in Catalysis, Vol. 26, Nos. 1-4, p. 21 (2003) and Vandu et al., Chem. Eng. Technol. Vol. 28, No. 9, p. 998 (2005)). It is also known that this increased hold-up can be counteracted to some extent by increased solids loading. Krishna et al. (2003) has shown that solids promote the coalescence of small bubbles to form larger bubbles. The rise velocity of larger bubbles is higher than that of smaller bubbles, resulting in a reduced gas residence time and gas hold-up. This coalescence mechanism will however have a limit beyond which further solids addition will not be as effective to reduce gas hold-up, as the population of small bubbles will already be small. In line with this expectation, Vandu et al. (2005) found that for gas velocities above 0.4 m/s, the gas hold-up is reduced by increasing the solids volume fraction in the degassed slurry up to a value of 0.2, after which no significant reduction in gas hold-up is noted. The converse of this observation is of course that a substantial increase is expected in the gas hold-up if the solids concentration or loading is decreased below a volume fraction of 0.2 when the gas velocity is higher than 0.4 m/s.

In line with the prior art references above, Luo et al. (Luo et al., AIChE Journal, Vol. 45, No. 4, p. 665 (1999)) and Behkish et al. (Behkish et al., Chem. Eng. Journal, Vol. 115, p. 157 (2006)) found that the gas hold-up increases with increasing gas velocity, increasing pressure and decreasing solids loading.

The expectation of a skilled person is consequently that operating a slurry bubble column at the combination of high gas velocity, low solids loading (below 20%) and high pressure when high single reactor capacity is being aimed for is not desirable as a result of the expected excessive gas hold-up and the obvious effect of low catalyst loading on reaction kinetics and thus on productivity. The excessive gas hold-up will also have adverse consequences for (amongst others) the removal of heat from the reactor and (if present) the internal liquid-catalyst separation system. In extreme cases of very high gas hold-ups, the gas rather than the slurry will become the continuous phase, resulting in a regime transition from a slurry bubble column reactor to a gas fluidised reactor suspending or transporting slurry droplets.

The prior art therefore teaches that it is not possible to increase the single reactor capacity of a slurry bubble column reactor further by increasing the gas velocity beyond a certain point. There is an expectation that the combination of a high gas velocity and a high operating pressure will lead to excessive gas hold-ups, especially when the solids concentration of the slurry is lower than 20 volume %, even more so when the solids concentration is 14 volume % or lower.

According to the invention, there is provided a process for producing at least one product from at least one gaseous reactant, the process including feeding said at least one gaseous reactant, as a gaseous feed or as part of a gaseous feed which is at an inlet superficial gas velocity of at least 0.5 m/s, into a vessel holding an expanded slurry bed of solid catalyst particles suspended in a suspension liquid so that the gaseous reactant can bubble upwardly through the slurry bed, the slurry bed having a catalyst loading of less than 14% by volume of degassed slurry;

allowing said at least one gaseous reactant to react catalytically at a pressure above atmospheric pressure as the gaseous reactant bubbles upwardly through the slurry bed to produce said at least one product; and withdrawing said at least one product and any unreacted gaseous reactant from the vessel.

In this specification, the term "inlet superficial gas velocity" is meant to imply the total gas inlet volumetric flow rate of the gaseous feed made up by, or which includes said at least one gaseous reactant at the slurry bed temperature and pressure where the gaseous feed enters the vessel, typically at a low level in the bottom of the slurry bed, divided by the cross-sectional area of the vessel, excluding any cross-sectional area that may be occupied by vessel internals, e.g. a gas distributor or cooling coils. In the event that multiple gaseous feeds are employed, the term "total gas inlet volumetric flow rate" is meant to imply the sum of all gas streams entering the reactor, i.e. the sum of all fresh gaseous feed streams and any gaseous recycle streams that may be present.

The product may include one or more gaseous products. The process may thus include allowing gaseous product and unreacted gaseous reactant to disengage from the slurry bed as gaseous components into a head space above the slurry bed. Withdrawing said at least one product and any gaseous reactant typically then includes withdrawing gaseous components from the head space.

The product may include one or more liquid products. The suspension liquid of the slurry bed may be fully or partially comprised of the liquid product. Withdrawing said at least one product and any unreacted gaseous reactant typically then includes withdrawing liquid phase from the slurry bed, thereby to maintain the expanded slurry bed at a desired level.

The process may include feeding more than one gaseous reactant into the slurry bed. In one embodiment of the invention, the gaseous feed includes at least CO and $H_2$ as gaseous reactants and the gaseous feed is thus fed into the slurry bed to produce liquid and gaseous hydrocarbons, with the catalyst being a hydrocarbon synthesis catalyst. Oxygenates may possibly also be produced from the gaseous reactants being fed into the slurry bed. The process may thus be a hydrocarbon synthesis process converting a synthesis gas feed to liquid and gaseous products with the liquid product and gaseous product including products typical of Fischer-Tropsch synthesis such as $C_3+$ hydrocarbons and oxygenates, e.g. ethanol. In one embodiment of the invention, the process is thus a Fischer-Tropsch hydrocarbon synthesis process converting synthesis gas into hydrocarbons.

The process may include limiting the per pass conversion of said at least one gaseous reactant, e.g. to less than 85 mol %. When the catalyst is a hydrocarbon synthesis catalyst and the gaseous feed includes CO and $H_2$, e.g. when the gaseous feed is synthesis gas, the per pass conversion of $CO+H_2$ may be limited to a value between about 35 and 85 mol %. The reason for this limit is that a high water concentration (water is a product of the hydrocarbon synthesis) is detrimental to the catalyst. The exact value of this conversion limit is determined by the characteristics of the catalyst and its tolerance for water, but normally a hydrocarbon synthesis process will operate at the highest per pass conversion where the catalyst has an acceptable activity, selectivity and lifetime. Cobalt catalysts are known for a high resistance to water partial pressure and will typically operate towards the upper boundary of said range, whereas iron catalysts are less tolerant to water and will typically operate towards the lower boundary of said range. With reference to Equation 2 and accompanying discussion, this per pass conversion limit plays a vital role in determining the single reactor capacity, irrespective of the activity of the catalyst. Therefore, a low activity catalyst with a high water tolerance may not be able to sustain a high production rate per reactor volume, but will in principle allow for a high single reactor capacity by increasing the reactor height; consequently a small number of tall reactors will be required in order to achieve the desired total production capacity of the plant. On the other hand, a highly active catalyst with a low water tolerance may sustain a very high production rate per reactor volume, but will not allow for a high single reactor capacity, since increasing the reactor height will lead to excessive conversions that will destroy the catalyst. Consequently, a large number of short reactors will be required in order to achieve the desired overall production capacity of the plant, which is also not a desirable situation.

Nevertheless, despite these limitations, it has surprisingly been found that the present invention enables a high single reactor capacity, even when the per pass syngas conversion is lower than 85 mol %, more surprisingly even when the syngas conversion is lower than 60 mol %, even more surprisingly even when the syngas conversion is lower than about 50 mol %, and most surprisingly even when the syngas conversion is lower than about 40 mol %. This is achieved by increasing the inlet superficial gas velocity to at least 0.5 m/s, more preferably to at least 0.6 m/s, even more preferably to at least 0.7 m/s, most preferably to at least 0.85 m/s, which high inlet superficial gas velocities were previously believed to be ineffective in increasing the single reactor capacity and ineffective in countering the effect of low catalyst loading on single reactor capacity due to an excessive gas hold up.

Typically, the inlet superficial gas velocity is less than 1.1 m/s, or even higher at less than 1.2 m/s; the inlet superficial gas velocity is typically not expected to be above 1.5 m/s.

The process may include feeding a recycle gas stream which includes unreacted gaseous reactant(s) from the head space to the slurry bed. Often, the recycle stream is combined with a fresh synthesis gas feed stream to form one total feed stream, i.e. said gaseous feed, to the reactor. As will be appreciated, the gaseous reactant(s) and any recycled gas and any gaseous product assist in maintaining the solid catalyst particles in suspension in the suspension liquid.

The catalyst loading may be less than 12% by volume of degassed slurry, possibly even less than 10% by volume of degassed slurry. Typically however, the catalyst loading will be at least 2% by volume of degassed slurry.

The slurry bed may be at a pressure of at least 10 bar, preferably at least 20 bar, more preferably at least 25 bar. The slurry bed may be at a pressure of up to about 60 bar.

The expanded slurry bed may have a height of less than about 40 m, preferably between about 30 m and about 40 m, e.g. about 38 m. Typically, the slurry bed has a diameter of at least 6 m. Thus, in one embodiment of the invention, the expanded slurry bed has a height of less than 40 m and a diameter of at least 6 m.

Typically, when the process is a hydrocarbon synthesis process, the process is a single stage process, i.e. the process comprises operating at least one multi-pass hydrocarbon synthesis stage with the multi-pass hydrocarbon synthesis stage not being followed or preceded by another hydrocarbon synthesis stage, although naturally the process may include a plurality of the multi-pass hydrocarbon synthesis stages in parallel. Thus, taking into account the limited per pass conversion of reactant(s), the recycle gas stream is typically present when the process is a hydrocarbon synthesis process and is typically being fed into the slurry bed at a volumetric ratio of recycle gas stream/gaseous feed of at least 0.4.

When the process is a hydrocarbon synthesis process, the catalyst may be a Fischer-Tropsch catalyst containing cobalt or iron. Cobalt-based catalysts are usually supported catalysts. Suitable supports include refractory inorganic oxides such as alumina, silica, titania, zirconia, and others known to those skilled in the art. Catalysts prepared on modified supports, such as those disclosed in U.S. Pat. Nos. 6,262,132, 6,638,889 and 6,117,814, are especially suitable for use in slurry bubble column reactors operated in accordance with the process of the invention. The catalyst particles may have a desired particle size range, e.g. no catalyst particles greater than 300 microns and less than 5% by mass of the catalyst particles being smaller than 22 microns.

Typically, when the process is a hydrocarbon synthesis process, the $H_2/CO$ molar ratio in the gaseous feed is an important parameter that can vary from about 0.5 to 2.5. It is known that a higher $H_2/CO$ ratio generally may have the benefit of an improved catalyst lifetime, whereas a lower $H_2/CO$ ratio may yield better product selectivities. Therefore, the $H_2/CO$ ratio of the gaseous feed is selected on the basis of an optimisation exercise of the process, and depends on aspects such as the catalyst characteristics, the desired product selectivities, etc. In preferred embodiments, the hydrocarbon synthesis process is operated with an $H_2/CO$ molar ratio of not more than 2. In other words, there is an excess CO above the stoichiometric requirements for hydrocarbon synthesis.

It is to be appreciated that the gaseous feed typically includes inert and diluent gases, such as $N_2$, particularly when the gaseous feed is synthesis gas. Another gas typically present in the gaseous feed is $CO_2$, which can be considered for all practical purposes to be an inert gas. As is known to those skilled in the art, although these inert or diluent gases are undesirable, they are sometimes inevitably present because it would be uneconomical to attempt to avoid or remove these gases. In other cases, such as when the synthesis gas is derived from coal via gasification, there is such a substantial quantity of $CO_2$ in the feed that it is often desirable to remove the $CO_2$ partially or completely from the fresh feed.

The process may include cooling the gaseous components from the head space to condense liquid product, e.g. liquid hydrocarbons and reaction water, separating the liquid product from the gases to provide a tail gas, and recycling at least some of the tail gas to the slurry bed as the recycle gas stream.

The slurry vessel may thus be maintained at normal elevated pressure and temperature conditions associated with Fischer-Tropsch synthesis reactions, e.g. a predetermined or selected operating pressure in the range 10 to 50 bar, and a predetermined or selected temperature in the range 160° C. to 280° C., or even higher for the production of lower boiling point product. Typically, for Fischer-Tropsch hydrocarbon synthesis, the temperature range is 200° C. to 260° C.

The catalyst particles in the slurry bed are thus maintained in suspension by the turbulence created by the gaseous feed (e.g. fresh synthesis gas and optional recycled gas) passing through the slurry bed, i.e. bubbling through the slurry bed. The inlet superficial gas velocity of at least 0.5 m/s through the slurry bed is thus sufficiently high to maintain the slurry bed in a state of turbulence or suspension.

The process may include recycling the liquid phase through the slurry bed. In particular, the process may include allowing slurry to pass downwardly from a high level in the slurry bed to a lower level thereof, using slurry redistribution means or slurry redistributors, thereby to redistribute heat, liquid phase and catalyst particles within the slurry bed.

In this specification, the term "slurry redistribution means" or "slurry redistributors" is intended to refer to physical apparatus used to redistribute slurry and catalyst particles vertically inside the reactor vessel, and does not refer to the slurry and catalyst particle redistribution action of the gas passing upwards through the slurry bed. The slurry redistribution means may thus include downcomers or draught tubes or mechanical redistribution apparatus such as pipes and pumps and filters.

When the slurry redistribution means includes downcomers, the downcomers may be arranged in a first downcomer region and a second downcomer region, with the second downcomer region being vertically spaced with respect to the first downcomer region.

The downcomers or draught tubes may thus be located at different levels or vertical elevations within the slurry bed. The second downcomer region may be located at a higher level than the first downcomer region, and, if desired, further downcomer regions, each containing at least one downcomer or draught tube may be provided above the second downcomer region, with a third and any subsequent downcomer regions also being spaced vertically from one another.

In one embodiment of the invention, the second downcomer region may overlap the first downcomer region. In other words, the lower end(s) of the downcomer(s) in the second downcomer region may overlap the upper end(s) of the downcomer(s) in the first downcomer region. In another embodiment of the invention, however, the second downcomer region may be located in non-overlapping relationship with respect to the first downcomer region. In other words, the lower end(s) of the downcomer(s) in the second downcomer region may be spaced with vertical clearance from the upper end(s) of the downcomer(s) in the first downcomer region.

The downcomer(s) in the second downcomer region may be staggered with respect to that (those) in the first downcomer region, when the reactor or vessel is seen in plan view. In other words, the lower end(s) of the downcomer(s) in the second downcomer region preferably does(do) not discharge slurry directly above the upper end(s) of the downcomer(s) in the first downcomer region.

Each downcomer may comprise a lower transport section and an upper disengagement or degassing section of greater cross-sectional area than the transport section. The sections are preferably circular in cross-section, is of cylindrical form, with an outwardly upwardly flaring connecting component connecting the disengagement section to the transport section. However, the disengagement section can, if desired, be in another suitable form, e.g. in the form of a rectangular or triangular section channel, as determined by the space available inside the reactor vessel.

While each downcomer will normally be located entirely within the slurry bed i.e. inside the reactor vessel, with the degassing section typically aligned axially with the transport section, the transport section and, optionally, part of the degassing section can, instead, be located outside the reactor vessel, with the lower outlet end of the transport section and at least the upper inlet end of the degassing section then, however, being located inside the reactor vessel in the slurry bed or the slurry bed zone. If desired, the transport and degassing sections may be cooled by indirect cooling means, for example, pipes through which boiler feed water is passed.

The process may include operating the hydrocarbon synthesis stage such that the slurry bed is in a heterogeneous or churn-turbulent flow regime and comprises a dilute phase consisting of fast-rising large voids of gaseous reactants, and possibly gaseous product, which traverse the expanded slurry bed virtually in a plug flow manner, and a dense phase comprising liquid phase, i.e. liquid product, solid catalyst particles, and entrained smaller voids of gaseous reactants and, possibly, gaseous product.

The gaseous feed may be any synthesis gas derived from any source, such as coal-derived synthesis gas or natural gas derived synthesis gas.

The ratio of recycle gas stream/gaseous feed may be in a range with a lower limit of 0.4 as hereinbefore indicated, with an upper limit of the range being about 1.5. The lower limit may however be higher at about 0.5, or even higher at about 0.6.

The upper limit may be lower at about 1.3, or even as low as about 1.

The invention will now be described and illustrated in more detail with reference to the experiments set out below and the accompanying diagrammatic drawings.

EXPERIMENT 1

Gas Hold-Up Measurements

Figure 1:
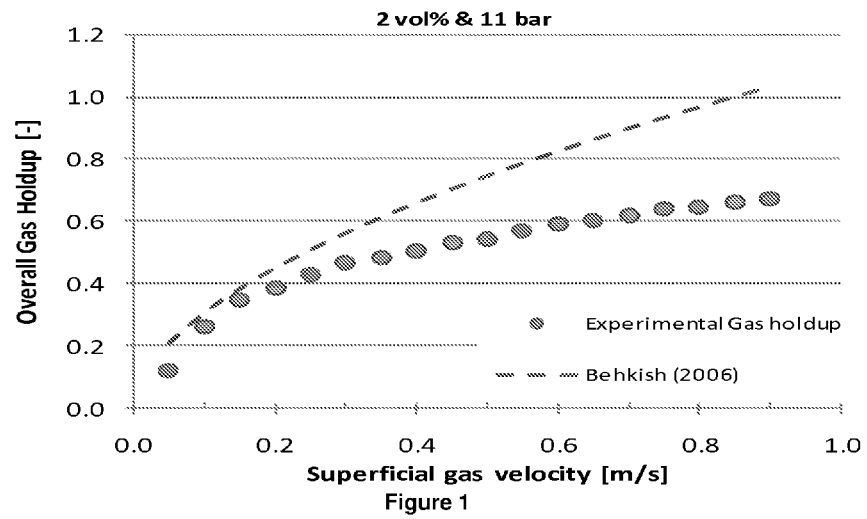
FIG. 1 shows a graph of predicted increase in gas hold-up with the correlation by Behkish (2006) as a function of gas velocity for a paraffin mixture containing 2 volume % solids, at a column pressure of 11 bar.

Gas hold-up measurements were performed in a cold model experimental set-up comprising a high pressure slurry bubble column with an inner diameter of 15 cm and a total height of 412 cm. Ten sight glasses were positioned along the reactor height to enable visual inspection of the flow inside the column. Compressed air entered the column from the bottom via a plenum chamber and through a distribution plate having 84 holes of 0.6 cm diameter each. A backpressure regulator was fitted on a gas outlet of the column in order to control the pressure at the desired value. Measurements were performed at the prevailing ambient temperature, which was about 15° C. The overall gas hold-up was determined from the extent of bed expansion when air was bubbled through the bed, i.e. it was calculated as the difference between the bed height under flow conditions and the height of the static bed before introduction of air.

The density of air at the prevalent conditions of the cold model measurements (temperature of 15° C., pressure ranging from 1 to 11 bar) is compared to that of synthesis gas under typical Fischer-Tropsch synthesis conditions (temperature from 200° C. to 230° C., pressure from 20 to 40 bar) in Table 1. The range of gas densities applicable to the cold model studies covers the gas density of the Fischer-Tropsch synthesis over a broad range of operating conditions, ensuring equivalence between the current measurements and the gas hold-up that would be encountered in commercially representative Fischer-Tropsch slurry bubble column reactors.

TABLE 1

Gas densities in kg m$^{-3}$ of synthesis gas and air

| Synthesis gas Pressure (bar) | Typical synthesis gas[a] density at 200° C. | Typical synthesis gas[a] density at 230° C. | Air P (bar) | Air[b] density at 15° C. |
|---|---|---|---|---|
| 20 | 6.6 | 6.2 | 1 | 1.2 |
| 25 | 8.2 | 7.7 | 2 | 2.4 |
| 30 | 9.9 | 9.3 | 5 | 6.1 |
| 35 | 11.5 | 10.8 | 8 | 9.8 |
| 40 | 13.1 | 12.3 | 11 | 13.4 |

[a]Assumed synthesis gas composition: 60% $H_2$, 30% CO, 6% $CO_2$ and 4% $CH_4$
[b]Assumed air composition: 79% $N_2$, 21% $O_2$ The liquid employed during the experiments was a mixture of $C_{12}$ and $C_{13}$ paraffins which, at room temperature, reasonably approximates the physical properties of the liquid phase in a Fischer-Tropsch slurry reactor at operating conditions of 200° C. to 230° C. The solid phase was alumina particles in the size range of 50 to 150 µm having a skeletal density of 3420 kg/m$^3$ and a particle density of 1721 kg/m$^3$, which is a typical support for slurry phase Fischer-Tropsch catalysts.

Gas hold-up measurements were performed over a wide range of gas velocities, column pressures and solids content in the slurry. The gas velocity is defined as the volumetric flow rate of air at the prevailing temperature and pressure condition divided by the cross sectional area of the column.

Slurry bubble column reactors, like those used in the Fischer-Tropsch synthesis, typically operate in the churn turbulent flow regime. With increasing gas hold-up, there comes a point where the gas rather than the slurry becomes the continuous phase, resulting in a regime transition from a slurry bubble column reactor to a gas fluidised reactor suspending or transporting slurry droplets. Steynberg et al. (Steynberg et al., Studies in Surface Science and Catalysis Vol. 152, Chapter 2 (2004)) reported that the gas hold-up at the onset of this phase inversion is around 0.65 to 0.7. It is further reported that at a gas hold-up of around 0.8 to 0.9, the reactor transforms into a transported bed where the liquid is blown out of the reactor.

Figure 2:
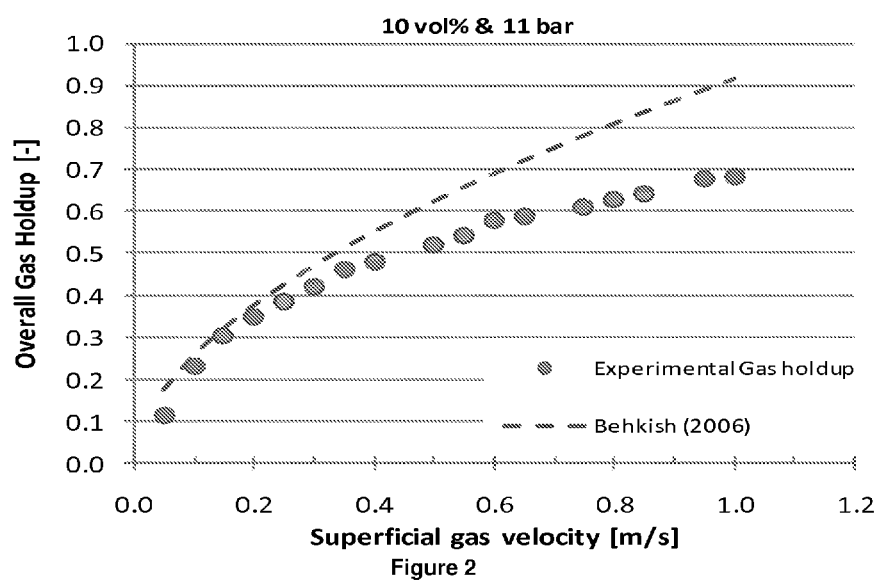
FIG. 2 shows a graph of predicted increase in gas hold-up with the correlation by Behkish (2006) as a function of gas velocity for a paraffin mixture containing 10 volume % solids at a column pressure of 11 bar.

Correlations in the prior art for predicting the gas hold-up in bubble column reactors have typically been developed for gas velocities of less than 0.4 m/s. Applying some of these correlations at conditions of high gas velocity, high pressure and low solids concentration result in predictions of excessive gas hold-up. For example, FIGS. 1 and 2 compare the gas hold-up correlation by Behkish (2006) as applied to the system of air/paraffin mixture/alumina particles (2 and 10 volume % particles in liquid, respectively, and a column pressure of 11 bar total pressure) to the measurements taken in this study. The correlation predicts excessive gas hold-ups of more than 0.8 when the gas velocity exceeds 0.6 m/s (FIG. 1). It even extrapolates to gas hold-up values higher than unity at gas velocities approaching 1 m/s, thereby exceeding a physical limit. Similar exaggerated gas hold-up values are predicted for higher solids loads as well (FIG. 2).

Figure 3:
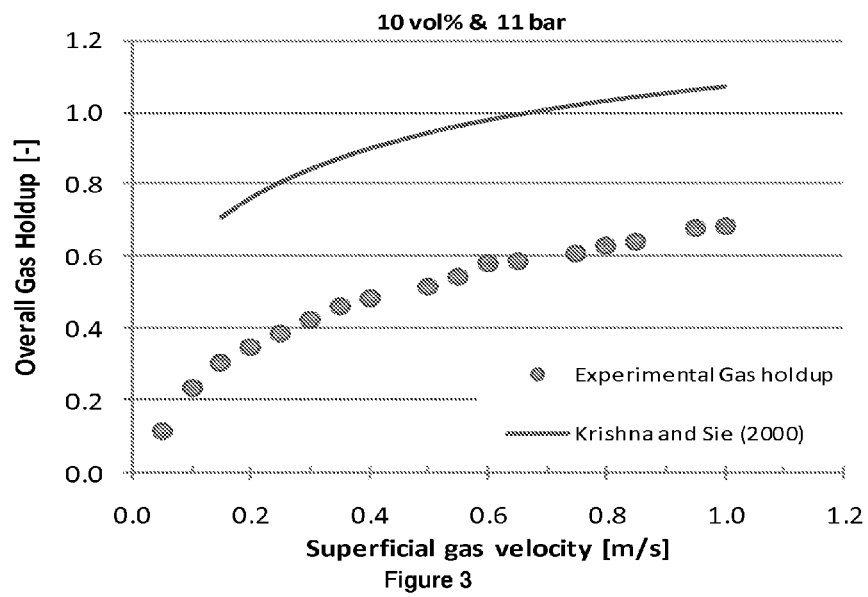
FIG. 3 shows a graph of predicted increase in gas hold-up with the correlation from Krishna and Sie (Krishna and Sie, Fuel Processing Technology, Vol. 64, p. 73 (2000)) as a function of gas velocity for a paraffin mixture containing 10 volume % solids at a column pressure of 11 bar.
Figure 4:
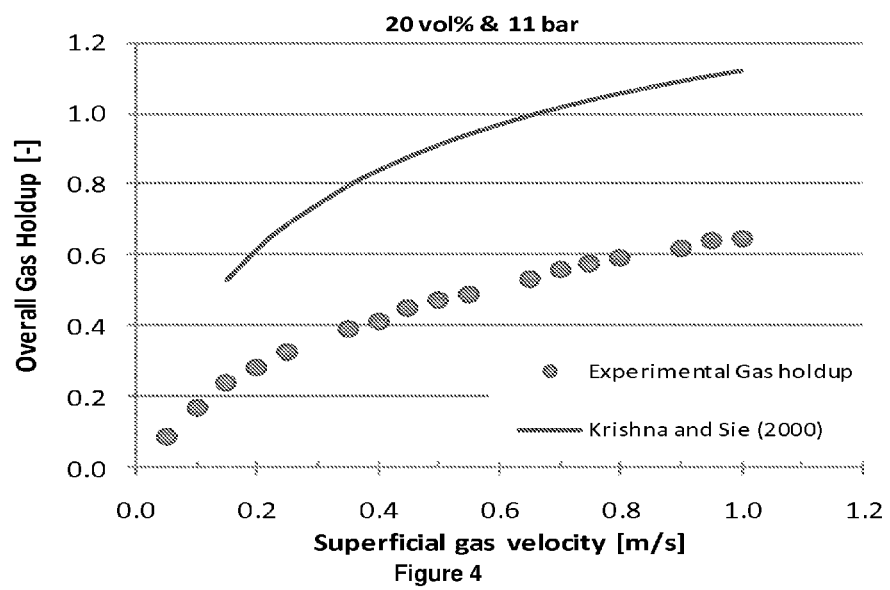
FIG. 4 shows a graph of predicted increase in gas hold-up with the correlation from Krishna and Sie (2000) as a function of gas velocity for a paraffin mixture containing 20 volume % solids at a column pressure of 11 bar.
Figure 5:
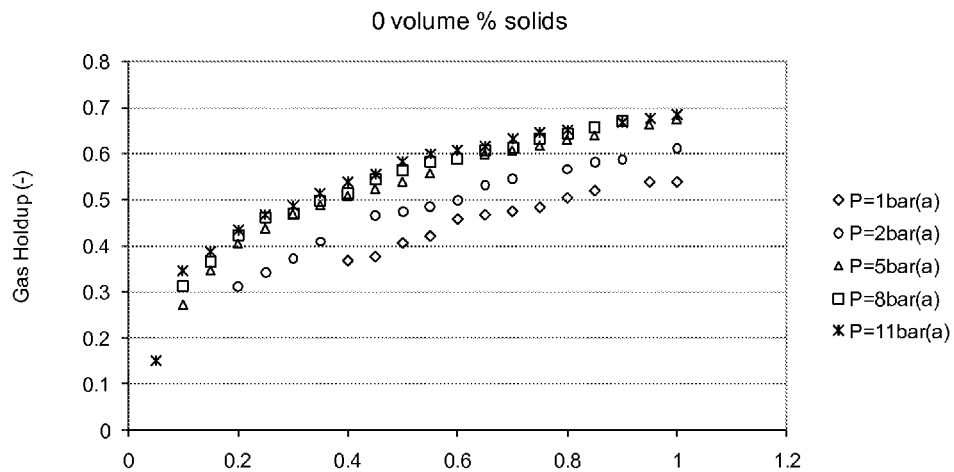
FIG. 5 shows a graph of gas hold-up as function of gas velocity and pressure, with no solids present.
Figure 6:
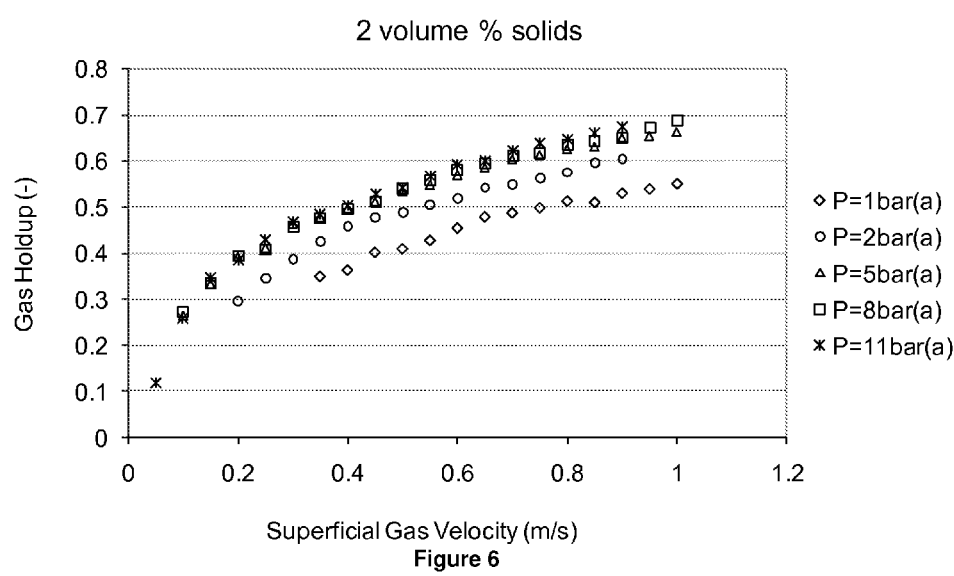
FIG. 6 shows a graph of gas hold-up as function of gas velocity and pressure, with 2 volume % solids present.
Figure 7:
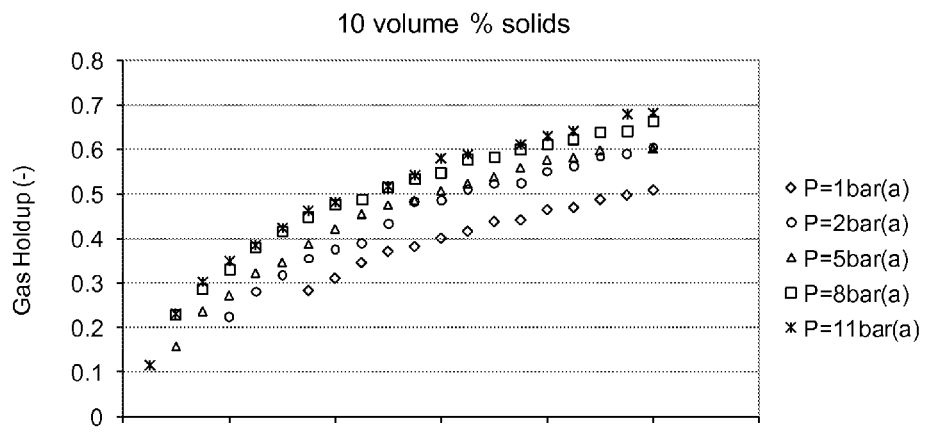
FIG. 7 shows a graph of gas hold-up as function of gas velocity and pressure, with 10 volume % solids present.
Figure 8:
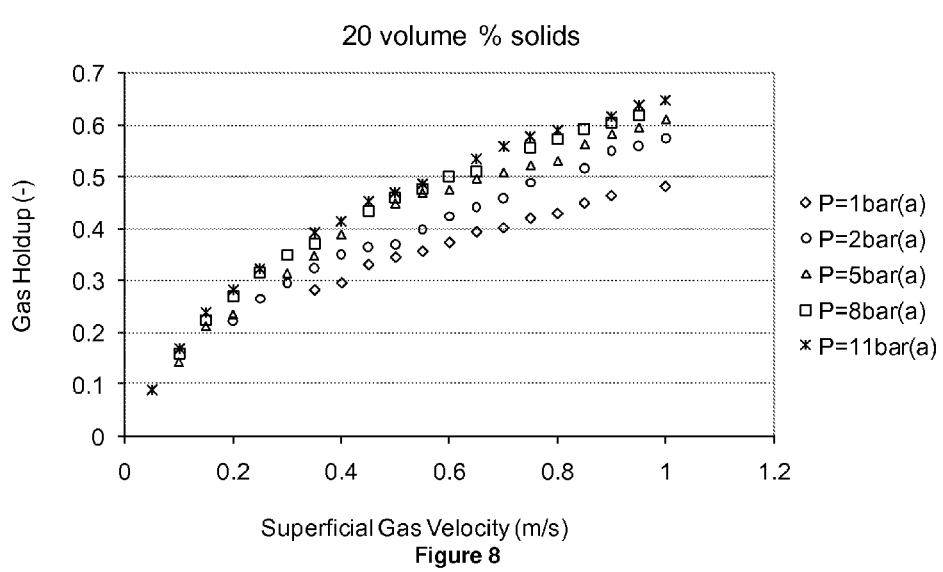
FIG. 8 shows a graph of gas hold-up as function of gas velocity and pressure, with 20 volume % solids present.

FIGS. 3 and 4 compare the gas hold-up correlation by Krishna and Sie (2000) as applied to the system of air/paraffin mixture/alumina particles (10 and 20 volume % particles in liquid, respectively, and a column pressure of 11 bar total pressure) to the measurements taken in this study. This correlation performs even worse, because the physical limit of a gas hold-up of unity is already exceeded at gas velocities around 0.6 m/s. Clearly the actual gas hold-up, as experimentally measured under these conditions, is substantially lower and within a range that will allow for adequate operation of a slurry bubble column reactor.

Based on the predictions of the prior art correlations, the skilled person would therefore anticipate a slurry bubble column to undergo phase inversion or even to transform into a transported bed under conditions of high gas velocity, high pressure and low solids concentration.

During the current study, gas hold-up measurements have been performed up to 1 m/s over a wide range of pressures (1 to 11 bar air, equivalent to more than 40 bar synthesis gas pressure in the case of the Fischer-Tropsch synthesis) and a wide range of slurry solids concentrations (0 to 20 volume %). The results, presented in FIGS. 5 to 8, indicate that a gas-hold-up of 0.65 has barely been exceeded, even under extreme conditions of high pressure and a liquid containing no solids. Not only are these gas hold-up values within the range associated with the churn-turbulent flow regime (according to Steynberg, (2004)), but also no hydrodynamic regime transitions were visually observed during any of the experiments.

EXPERIMENT 2

Mass Transfer Measurements

Figure 9:
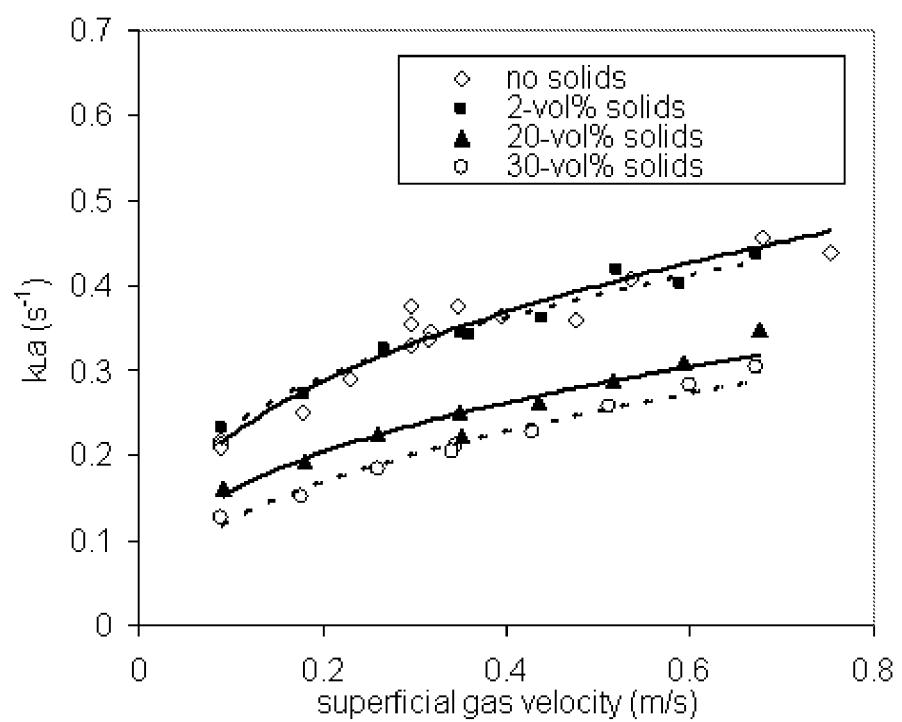
FIG. 9 shows a graph of mass transfer coefficients as obtained in current study at various gas velocities and solid loads.

Mass transfer measurements were performed in a cold model experimental set-up comprising a slurry bubble column with an inner diameter of 14 cm which operated at atmospheric pressure. The liquid employed during the experiments was a mixture of $C_{12}$ and $C_{13}$ paraffins which, at room temperature, reasonably approximates the physical properties of the liquid phase in a Fischer-Tropsch slurry reactor at operating conditions of 200° C. to 230° C. The solid phase was alumina particles, which is a typical support for slurry phase Fischer-Tropsch catalysts. Mass transfer measurements were performed over a wide range of gas velocities and for different solids concentrations. The gas velocity is defined as the volumetric flow rate of gas at the prevailing temperature and pressure condition divided by the cross sectional area of the column. The procedure was to establish a flow of pure nitrogen, at a certain gas velocity, through the column for a time sufficient to ensure that all oxygen was stripped from the liquid phase. Then, at a specific instant (defined as "time zero" or abbreviated to t=0), the nitrogen flow was replaced with an air flow at exactly the same gas velocity. Two oxygen sensors, placed at certain positions inside the column, then measured oxygen uptake into the liquid. The data were used to calculate the mass transfer coefficient at the involved gas velocity and solids concentration. The results of the study are presented in FIG. 9. It can be seen that decreasing the solids load from 30 to 20 volume % results in a very small increase in the mass transfer coefficient, but that a further decrease in the solids concentration from 20 to 0 volume % results in a substantial rise in the mass transfer coefficient.

The cold model results indicate that a combination of a high gas velocity and a low solids concentration unexpectedly results in acceptable gas hold-ups, even at high pressures. Also very high mass transfer coefficients are obtained at these conditions. This allow for both a high single reactor capacity and a high reaction rate per reactor volume.

In order to fully exploit the benefits of this invention, one should ideally operate the process under conditions where fast reaction kinetics is favoured. This can be achieved by using a high activity catalyst, or by operating at high temperatures and pressures which are conducive to high reaction rates.

Figure 10:
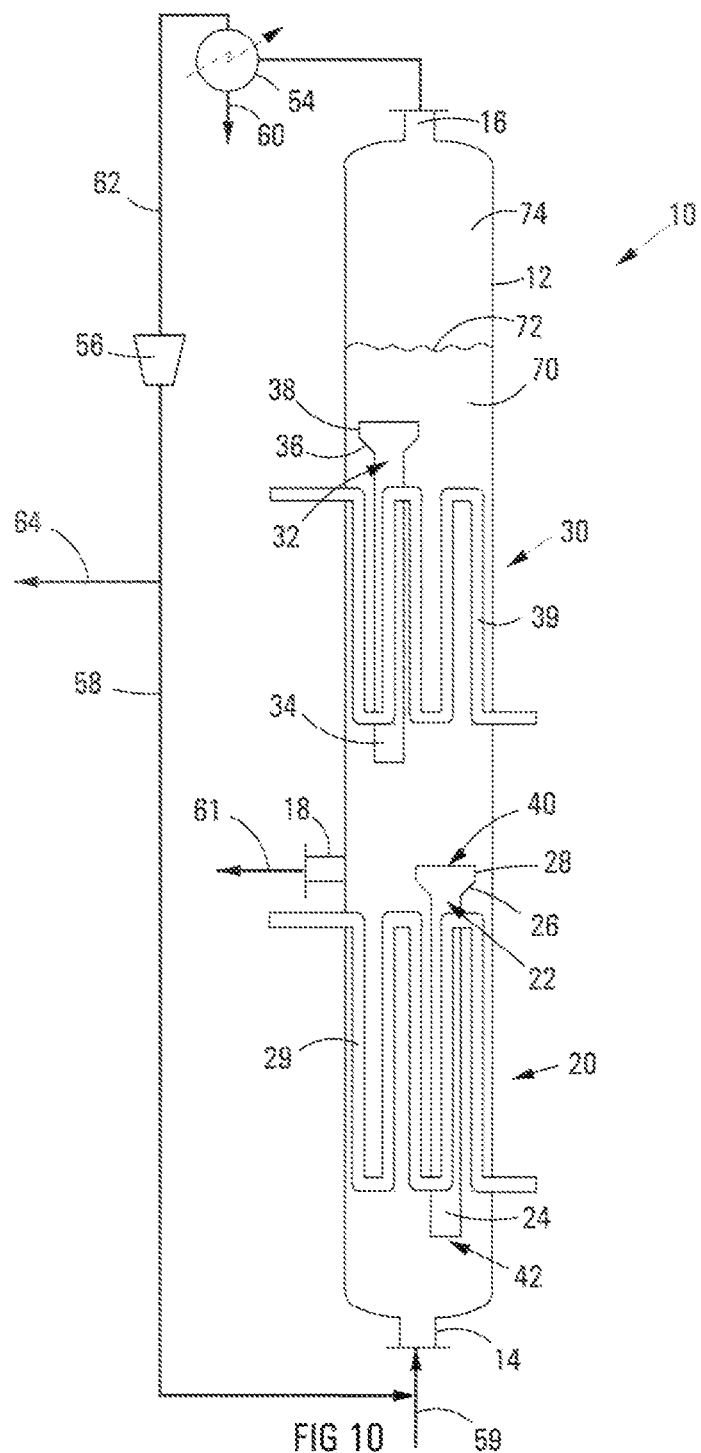
FIG. 10 shows a longitudinal sectional view of an installation which can be used in a process in accordance with the invention for producing at least one product from at least one gaseous reactant in a slurry bed.

Referring to FIG. 10, reference numeral 10 generally indicates an installation for Fischer-Tropsch hydrocarbon synthesis.

The installation 10 includes an upright circular cylindrical Fischer-Tropsch synthesis slurry phase reactor or bubble column 12, with a bottom gaseous reactants feed inlet 14 leading into a gas distributor (not shown) inside the reactor 12 and a gaseous components outlet 16 leading from the top of the reactor 12. A liquid phase product outlet 18 leads from the reactor 12 at any convenient level.

The reactor 12 includes a first downcomer region, generally indicated by reference numeral 20. The downcomer region 20 includes a downcomer, generally indicated by reference numeral 22. The downcomer 22 includes a cylindrical transport section 24 of relatively small diameter, an outwardly flaring connecting component 26 at an upper end of the transport section 24, and a larger diameter degassing section 28, a lower end of which is connected to the connecting component 26. An upper end of the degassing section 28 thus provides an inlet 40 for slurry, while a lower end of the transport section 24 provides a slurry outlet 42. Cooling pipes 29 are also provided in the downcomer region 20.

The reactor 12 also includes a second downcomer region, generally indicated by reference numeral 30. The downcomer region 30 includes a downcomer, generally indicated by reference numeral 32. The downcomer 32 also includes a transport section 34 of relatively small diameter, an outwardly flaring connecting component 36 at an upper end of the transport section 34, and a degassing section 38 of relatively large diameter at an upper end of the transport section 34. A lower end of the degassing section 38 is thus connected to the connecting component 36. An upper end of the degassing section 38 provides a slurry inlet, while a lower end of the transport section 34 provides a slurry outlet. Cooling pipes 39 are also provided in the downcomer region 30.

The lower end of the downcomer 32 is spaced with vertical clearance from the upper end of the downcomer 22. Furthermore, the downcomer 32 is not aligned axially with the downcomer 22. In other words, the downcomer 32 is staggered relative to the downcomer 22 when the reactor 12 is seen in plan view.

The installation 10 further includes a separation unit 54 in flow communication with the gaseous components outlet 16 and a compressor 56 in flow communication with the separation unit 54. A recycle gas stream line 58 leads from the compressor 56 to join a reactants feed line 59 going to the feed inlet 14. A liquid product line 60 leads from the separation unit 54, with a tail gas line 62 establishing flow communication between the separation unit 54 and the compressor 56. A tail gas withdrawal line 64 splits off from the tail gas recycle line 58 and a further liquid product line 61 leads from the liquid phase product outlet 18.

The reactor 12 in use provides a slurry bed zone containing a slurry bed 70 comprising about 10-14% by volume of hydrocarbon synthesis supported cobalt catalyst particles suspended in liquid phase product. The slurry bed 70 has an upper surface at a normal level 72 above the second downcomer region 30, with a head space 74 being provided above the slurry bed 70.

In use, a gaseous reactants feed or fresh synthesis gas comprising mainly carbon monoxide and hydrogen as gaseous reactants, is fed into the bottom of the reactor 12 through the reactants feed line 59 and the gaseous reactants feed inlet 14, the gas typically being uniformly distributed through a sparger system or grid plate (not shown) inside the reactor 12. Simultaneously, a recycle gas stream (typically cooled) comprising typically hydrogen, carbon monoxide, methane and carbon dioxide is returned to the reactor 12 through the recycle gas stream line 58.

The gaseous reactants, comprising the fresh synthesis gas and the recycled gas, pass upwardly through the slurry bed 70. As the synthesis gas bubbles through the slurry bed 70, the gaseous reactants therein react catalytically to form liquid product, which thus forms part of the slurry bed 70. From time to time, or continuously, liquid phase comprising liquid product is withdrawn through the liquid phase product outlet 18 and the liquid product line 61, with catalyst particles being separated from the liquid product in a suitable internal or external separation system, e.g. using filters (not shown). If the separation system is located externally to the reactor, an additional system (not shown) to return the separated catalyst particles to the reactor is then provided.

The gaseous reactants feed (fresh synthesis feed gas) and the recycled gas are introduced into the bottom of the reactor 12 at a rate sufficient to agitate and suspend all of the catalyst particles in the system without settling. The gas flow rates will be selected depending on the slurry concentration, catalyst density, suspending medium density and viscosity, and particular particle size used. However, in accordance with the invention, the gas flow rates are selected such that the gases pass upwardly through the slurry bed 70 at an inlet superficial gas velocity of at least 0.5 m/s in a bottom end region of the reactor 12 where the gas enters the slurry bed 70.

Some slurry continuously passes downwardly through the downcomers 32, 22 thereby to achieve uniform redistribution of catalyst particles within the slurry bed 70, and also to ensure uniform heat distribution throughout the slurry bed 70.

The reactor 12 is operated so that the slurry bed 70 thereof is in a heterogeneous or churn-turbulent flow regime and comprises a dilute phase consisting of fast-rising larger voids of gaseous reactants and gaseous product which traverse the slurry bed 70 virtually in plug flow fashion and a dense phase which comprises liquid product, solid catalyst particles and entrained smaller voids of gaseous reactants and gaseous product which are back-mixed.

Boiler water as an indirect heat exchange or heat transfer medium is circulated through the coolant pipes 29, 39. Heat is transferred from the slurry bed 70 to the boiler water to form a mixture of steam and water.

Light hydrocarbon products, such as a $C_{19}$ and below fraction is withdrawn from the reactor 12 through the gaseous components outlet 16 and passed to the separation unit 54. Typically, the separation unit 54 comprises a series of coolers and a vapour-liquid separator and may optionally include further coolers and separators, and possibly also a cold separation unit, for separation of liquid phase light hydrocarbon products, water and optionally carbon dioxide from the remaining gaseous components. Other separation technologies such as membrane units, pressure swing adsorption units and/or units for the selective removal of carbon dioxide and methane may be employed. The separated gases comprising hydrogen, carbon monoxide and other gases are compressed and recycled by means of the compressor 56 to provide the recycle gas stream in the recycle gas stream line 58. A tail gas stream is withdrawn by means of the tail gas line 64 to prevent build up of inerts in the reactor 12. Condensed liquid hydrocarbons and reaction water are withdrawn from the separation unit 54 by means of the flow line 60 for further working up.

In accordance with a preferred embodiment of the invention, the recycle gas stream 58 is fed to the slurry bed 70 through the recycle gas stream line 58 and the inlet 14 at a volumetric ratio of recycle gas stream in line 58/gaseous reactants feed coming in through the gaseous reactants feed line 59, of at least 0.4. Thus, the process 10 employs a multi-pass hydrocarbon synthesis stage defined by the reactor 12, making use of a relatively large recycle ratio.

The reactor vessel 12 is typically maintained at an operating pressure of between about 10 bar and about 50 bar, more typically between about 20 bar and about 30 bar, and at an operating temperature of between 160° C. and 280° C., typically between about 200° C. and 260° C., e.g. between 200° C. and 230° C. The operating pressure and the operating temperature selected may depend on the nature and spread of gaseous and liquid product required and the type of catalyst used. Naturally, the reactor vessel 12 is provided with suitable temperature control means, such as the coolant pipes 29, 39 for controlling the reaction temperatures, as well as suitable pressure control means such as one or more pressure control valves (not shown).

In the reactor vessel 12, as the synthesis gas passes through the slurry bed 70, the carbon monoxide and hydrogen react to form a range of products in accordance with known Fischer-Tropsch reactions. Some of these products are in gaseous form at the operating conditions of the reactor 12, as mentioned hereinbefore, and are withdrawn as gaseous components through the gaseous components outlet 16, as also mentioned hereinbefore. Some of the products produced are in liquid form, e.g. waxes, at the operating conditions of the reactor 12, and act as the suspension medium for the catalyst particles, as also mentioned hereinbefore.

Despite the prejudice in the prior art, the inventors have surprisingly found that the operation of a slurry bubble column reactor with a combination of a high gas inlet superficial velocity, high pressure and low solids concentration in the slurry does not lead to excessive gas hold-up. This creates an opportunity to design slurry reactors with higher single reactor capacities than was possible before, since a low solids concentration in the slurry favours high mass transfer coefficients that are desirable to sustain a high conversion rate of reactants.

The invention claimed is:

1. A process comprising
feeding at least one gaseous reactant, as a gaseous feed or as part of a gaseous feed which is at an inlet superficial gas velocity of at least 0.5 m/s but no more than 1.5 m/s, into a vessel holding an expanded slurry bed of solid catalyst particles suspended in a suspension liquid so that the gaseous reactant can bubble upwardly through the slurry bed, the slurry bed having a catalyst loading of less than 14% by volume but at least 2% by volume of degassed slurry;
allowing said at least one gaseous reactant to react catalytically at a pressure above atmospheric pressure as the gaseous reactant bubbles upwardly through the slurry bed to produce at least one product; and
withdrawing said at least one product and any unreacted gaseous reactant from the vessel.

2. The process as claimed in claim 1, in which the gaseous feed comprises at least CO and $H_2$ as gaseous reactants, and in which the gaseous feed is fed into the slurry bed to produce liquid and gaseous hydrocarbons, with the catalyst being a hydrocarbon synthesis catalyst.

3. The process as claimed in claim 1, in which the inlet superficial gas velocity is at least 0.6 m/s.

4. The process as claimed in claim 3, in which the inlet superficial gas velocity is at least 0.7 m/s.

5. The process as claimed in claims 1, in which the inlet superficial gas velocity is at least 0.85 m/s.

6. The process as claimed in claim 1, in which the per pass conversion of a synthesis gas as said gaseous feed or as part of said gaseous feed is lower than 85 mol %.

7. The process as claimed in claim 1, in which the catalyst loading is less than 12% by volume of degassed slurry.

8. The process as claimed in claim 7, in which the catalyst loading is less than 10% by volume of degassed slurry.

9. The process as claimed in claim 1, in which the expanded slurry bed has a height of less than 40 m and a diameter of at least 6 m.

10. A process comprising the steps of:
(a) feeding a gaseous feed, comprising a gaseous reactant, at an inlet superficial gas velocity of at least 0.5 m/s but no more than 1.5 m/s into a vessel holding an expanded slurry bed of solid catalyst particles suspended in a suspension liquid so that the gaseous reactant or plurality of gaseous reactants can bubble upwardly through the slurry bed, the slurry bed having a catalyst loading of less than 14% by volume but at least 2% by volume of degassed slurry;
(b) allowing said gaseous reactant to react catalytically at a pressure above atmospheric pressure as the gaseous reactant bubbles upwardly through the slurry bed to produce a desired product; and (c) withdrawing said product and any unreacted gaseous reactant from the vessel.

11. A process comprising the steps of:
(a) feeding a gaseous feed, comprising a plurality of gaseous reactants, at an inlet superficial gas velocity of at least 0.5 m/s but no more than 1.5 m/s into a vessel holding an expanded slurry bed of solid catalyst particles suspended in a suspension liquid so that the plurality of gaseous reactants can bubble upwardly through the slurry bed, the slurry bed having a catalyst loading of less than 14% by volume but at least 2% by volume of degassed slurry;
(b) allowing said plurality of gaseous reactants to react catalytically at a pressure above atmospheric pressure as the plurality of gaseous reactants bubble upwardly through the slurry bed to produce a plurality of products; and
(c) withdrawing said plurality of products and any unreacted gaseous reactant from the vessel.

* * * * *